United States Patent
Min et al.

(10) Patent No.: US 7,295,873 B1
(45) Date of Patent: Nov. 13, 2007

(54) ANTI-TACHYCARDIA PACING METHOD AND APPARATUS FOR MULTI-CHAMBER PACING

(75) Inventors: Xiaoyi Min, Thousand Oaks, CA (US); Gene A. Bornzin, Simi Valley, CA (US); Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 666 days.

(21) Appl. No.: 10/893,710

(22) Filed: Jul. 15, 2004

Related U.S. Application Data

(63) Continuation-in-part of application No. 10/045,495, filed on Oct. 19, 2001, now Pat. No. 6,907,286.

(51) Int. Cl.
*A61N 1/362* (2006.01)
(52) U.S. Cl. .................................... 607/14
(58) Field of Classification Search .......... 607/4–28
See application file for complete search history.

(56) References Cited

U.S. PATENT DOCUMENTS

| | | | |
|---|---|---|---|
| 4,181,133 A | 1/1980 | Kolenik et al. | 128/419 PG |
| 4,280,502 A | 7/1981 | Baker, Jr. et al. | 128/419 PG |
| 4,390,021 A | 6/1983 | Spurrell et al. | 128/419 PG |
| 4,398,536 A | 8/1983 | Nappholz et al. | 128/419 PG |
| 4,408,606 A | 10/1983 | Spurrell et al. | 128/419 PG |
| 4,488,553 A | 12/1984 | Nappholz et al. | 128/419 PG |
| 4,488,554 A | 12/1984 | Nappholz et al. | 128/419 PG |
| 4,686,988 A | 8/1987 | Sholder | 128/419 PT |
| 4,708,142 A | 11/1987 | DeCote, Jr. | 128/419 PT |
| 4,712,555 A | 12/1987 | Thornander et al. | 128/419 PG |
| 4,729,376 A | 3/1988 | DeCote, Jr. | 128/419 PG |
| 4,788,980 A | 12/1988 | Mann et al. | 128/419 PG |
| 4,940,052 A | 7/1990 | Mann et al. | 128/419 PG |
| 4,944,298 A | 7/1990 | Sholder | 128/419 PG |
| 4,969,467 A | 11/1990 | Callaghan et al. | 128/419 PG |

(Continued)

FOREIGN PATENT DOCUMENTS

EP 1304137 A2 4/2003

(Continued)

OTHER PUBLICATIONS

Bocchiardo, Mario et al., "*Efficacy of Biventricular Sensing and Treatment of Ventricular Arrhythmias,*" PACE, vol. 23 (Nov. 2000, Part II), pp. 1989-1991.

*Primary Examiner*—Scott M. Getzow

(57) ABSTRACT

Improved methods and devices perform tachycardia detection and anti-tachycardia pacing (ATP) to convert a tachycardia (e.g., VT or AT) to normal sinus rhythm. According to one embodiment, an anti-tachycardia pacing method includes sensing, during sinus rhythm, first and second cardiac signals at first and second sites, respectively, in a patient's heart. The first and second sites include left and right ventricles or left and right atria, for example. The method further includes sensing third and fourth cardiac signals at the first and second sites, respectively, during a tachycardia (e.g., ventricular tachycardia or atrial tachycardia). The cardiac signals are processed to provide respective values. One or more anti-tachycardia pacing pulses are delivered at the site closest to the reentrant circuit based on a comparison of a first ratio of the first and third values and a second ratio of the second and fourth values. Unipolar sensing of the cardiac signals may be employed by, for example, shorting together pairs of electrodes implanted at each site.

25 Claims, 4 Drawing Sheets

U.S. PATENT DOCUMENTS

| | | |
|---|---|---|
| 5,350,410 A | 9/1994 | Kleks et al. .................. 607/28 |
| 5,466,254 A | 11/1995 | Helland ...................... 607/123 |
| 5,573,550 A | 11/1996 | Zadeh et al. ................. 607/28 |
| 5,855,592 A | 1/1999 | McGee et al. ................. 607/4 |
| 5,865,838 A | 2/1999 | Obel et al. .................... 607/5 |
| 6,178,351 B1 | 1/2001 | Mower ........................ 607/5 |
| 6,314,406 B1 | 11/2001 | O'Hagan et al. ............. 605/14 |
| 6,337,995 B1 | 1/2002 | Mower ........................ 607/5 |
| 6,484,057 B2 | 11/2002 | Ideker et al. ................. 607/14 |

FOREIGN PATENT DOCUMENTS

| | | |
|---|---|---|
| WO | WO 00/41765 | 7/2000 |

ANTI-TACHYCARDIA PACING METHOD AND APPARATUS FOR MULTI-CHAMBER PACING

CROSS-REFERENCES TO RELATED APPLICATIONS

This application is a continuation-in-part of U.S. patent application Ser. No. 10/045,495, filed Oct. 19, 2001 now U.S. Pat. No. 6,907,286, entitled "Anti-Tachycardia Pacing Methods and Devices", which is incorporated herein by reference.

FIELD OF THE INVENTION

The present invention relates generally to implantable cardiac simulation devices and, more particularly, to tachycardia detection and anti-tachycardia pacing schemes.

BACKGROUND OF THE INVENTION

The heart is a series of pumps that are carefully controlled by a very special electrical system. This electrical system attempts to regulate the heart rate between 60 and 100 beats per minute. The initial electrical signal originates near the top of the upper chamber on the right side of the heart. This chamber is called the right atrium and the special tissue that generates the signal is called the sino-atrial or SA node.

The electrical signal continues in a downward fashion through the atrio-ventricular or AV node, where the signal is slowed slightly by special tissue. The AV node is the "doorway" or relay station to the bundle of His (pronounced Hiss), and the bundle branches in the lower chambers of the heart.

After passing through the left and right bundle branches, the impulse arrives at the Purkinje fibers, where it is transmitted to the muscle cells of the left and right ventricles. Because of the specialized way in which the impulse is transmitted, the ventricles contract almost simultaneously.

With normal conduction, the cardiac contractions are very organized and timed so that the top chambers (the atria) contract before the lower chambers and the heart rate is maintained between 60 and 100 beats per minute.

Abnormally fast heart rates are called tachycardias. As used herein, the term tachycardia means a heartbeat at a rate which is abnormally high and accordingly considered to be dangerous if permitted to continue, or any arrhythmia involving recognizable heartbeat patterns containing repetitions which are in excess of a periodic heartbeat within a safe range.

When the ventricular chambers beat too quickly, the arrhythmia (i.e., unusual heart rhythm) is known as ventricular tachycardia. When ventricular tachycardia (VT) occurs, the ventricles may not be able to fill with enough blood to supply the body with the oxygen rich blood that it needs. Symptoms of VT include feeling faint, sometimes passing out, dizziness, or a pounding in the chest.

Ventricular tachycardia may be controlled by medication in some cases. If medications are not effective, the physician may elect to control the rhythm by electrical methods. The most common electrical therapy for VT is implantation of a device known as an Implantable Cardioverter Defibrillator (ICD). The ICD applies an electric shock to the heart muscle to interrupt or disrupt the fast rhythm. The electric shock may be in the form of specially timed pacemaker pulses (unfelt by the patient) or by high voltage shock. The high voltage shock, if required, is usually painful to the patient. Accordingly, it is preferential to use pacemaker pulses (also referred to as pacing pulses).

Tachycardias can result due to any number of reasons. For example, patients who have had myocardial infarctions, or other diseases that create scarring in the ventricular region of the heart, often develop monomorphic ventricular tachycardias. A monomorphic ventricular tachycardia (MVT) is a type of tachycardia that originates from one ventricular focus. These tachycardias often arise in and around the area of scarring on the heart. They are typically uniform and typically occur at a regular rate. Faster MVTs are often associated with hemodynamic compromise, whereas slower MVTs can be more stable.

Anti-Tachycardia Pacing (ATP) has been used to convert ventricular tachycardias into normal sinus rhythm. However, conventional ATP has not proved to be one hundred percent successful at returning the heart to normal sinus rhythm. Additionally, in a rare case, conventional ATP will accelerate the rhythm to ventricular fibrillation. Accordingly, improved methods and apparatuses for decreasing the failure rate of ATP are required. Some of the prior patent documents which teach ATP using low voltage shock therapy systems include U.S. Pat. No. 4,408,606; U.S. Pat. No. 4,398,536; U.S. Pat. No. 4,488,553; U.S. Pat. No. 4,488,554; U.S. Pat. No. 4,390,021; U.S. Pat. No. 4,181,133; and U.S. Pat. No. 4,280,502.

Tachycardia is often the result of electrical feedback within the heart; a natural beat results in the feedback of an electrical stimulus which prematurely triggers another beat. By interposing a stimulated heartbeat (i.e., a pacing pulse), the feedback loop may be disrupted. For example, patients with MVT can often times be successfully paced out of the tachycardia using a rapid burst of high rate pacing. The burst consists of a selected number of pulses all delivered at the same rate, an accelerating rate, or an alternating accelerating/decelerating rate. The mechanism that determines success of the burst is the ability to peel-back the refractories between the pacing site and the origin of the arrhythmia and penetrate the reentrant loop.

In conventional ATP, anti-tachycardia pacing pulses are delivered using two electrodes within the right ventricle (RV). It has been found that RV only ATP is clinically effective in terminating VT with 90% typical success rates. Clinical studies have indicated that simultaneous BV ATP is comparable to RV only ATP. See Bocchiardo et al., "Efficacy of Biventricular Sensing and Treatment of Ventricular Arrhythmias," PACE, Vol. 23, November 2000, pp. 1989-1991. In the Bocchiardo study, the BV pacing was accomplished using an RV tip electrode, an RV proximal electrode, and an LV tip electrode. The Bocchiardo study concluded that "[t]he success rates of spontaneous VT termination by BV ATP versus RV ATP were comparable."

BRIEF SUMMARY

Disclosed herein are embodiments including methods and devices for detecting tachycardia and performing anti-tachycardia pacing (ATP) to convert the tachycardia (e.g., VT or AT) to normal sinus rhythm.

According to one embodiment, an anti-tachycardia pacing method includes sensing, during sinus rhythm, first and second cardiac signals at first and second sites, respectively, in a patient's heart. The first and second sites may include left and right ventricles or left and right atria, for example. The method further includes sensing third and fourth cardiac signals at the first and second sites, respectively, during a tachycardia (e.g., ventricular tachycardia or atrial tachycardia). The first and second cardiac signals are processed to provide first and second values, respectively, and the third and fourth cardiac signals are processed to provide third and fourth values, respectively. The method further includes comparing a first ratio of the first and third values and a second ratio of the second and fourth values, and delivering one or more anti-tachycardia pacing pulses at one of said first and second sites based on said comparing of said first and second ratios. The method may employ unipolar sensing of the cardiac signals by, for example, shorting together pairs of electrodes implanted at each of the first and second sites.

Other embodiments are disclosed and claimed herein.

DETAILED DESCRIPTION

I. Exemplary Stimulation Device

Figure 1:
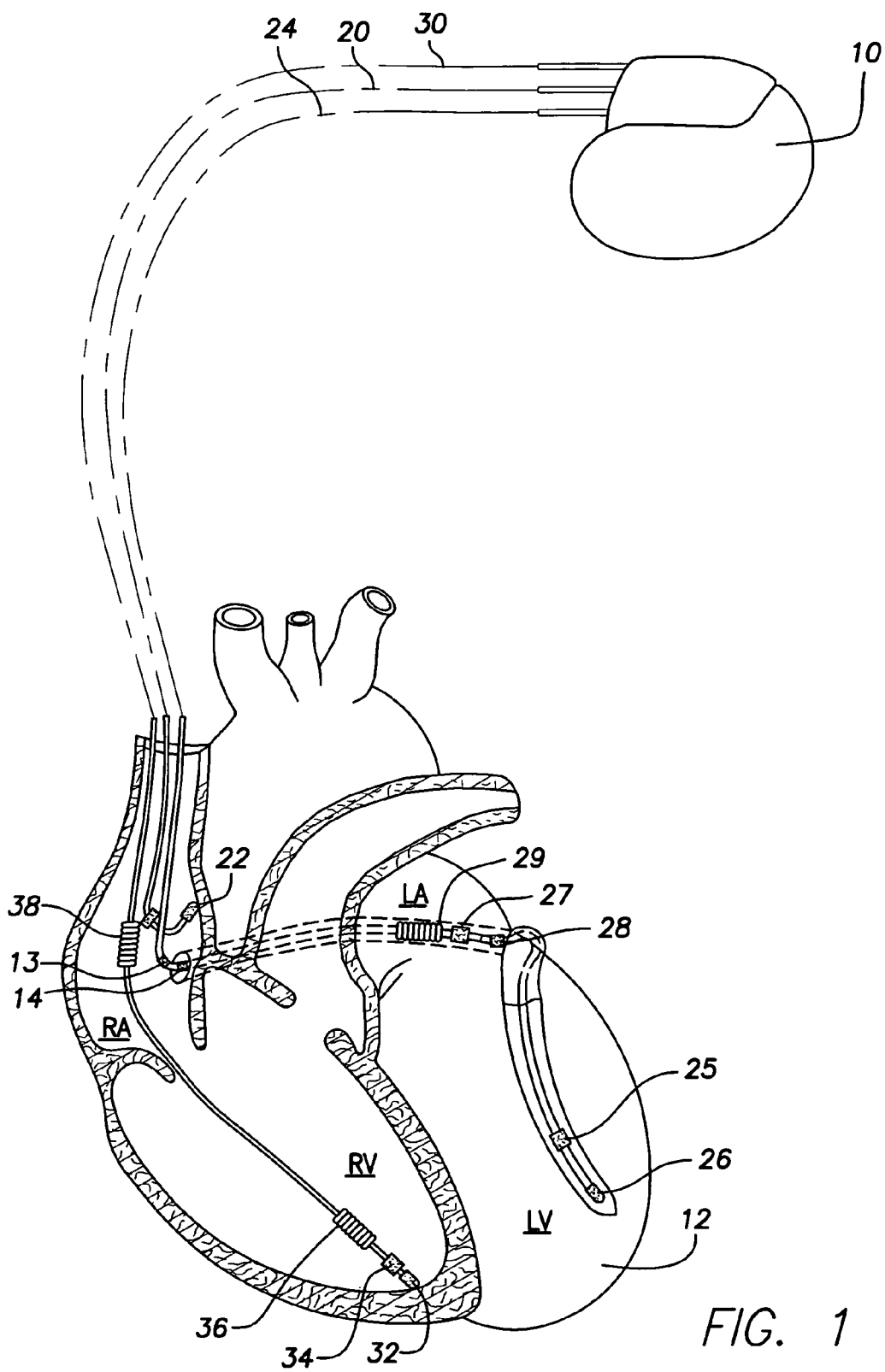
FIG. 1 is a simplified diagram illustrating an exemplary implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. Stimulation device 10 is also known as and referred to as a pacing device, a pacing apparatus, a cardiac rhythm management device, or an implantable cardiac stimulation device. Stimulation device 10 can be an implantable cardioverter/defibrillator (ICD).

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using a left ventricular (LV) tip electrode 26 and a LV ring 25. Left atrial pacing therapy uses, for example, first and second left atrial (LA) ring electrodes 27 and 28. Shocking therapy can be performed using at least a left atrial (LA) coil electrode 29. For a description of an exemplary coronary sinus lead, see U.S. Pat. No. 5,466,254, "Coronary Sinus Lead with Atrial Sensing Capability" (Helland), which patent is incorporated herein by reference. Coronary sinus lead 24 can also include a pair of right atrial (RA) rings 13 and 14 that may be used to provide right atrial chamber pacing therapy, as shown in FIG. 1.

The stimulation device 10 is also shown in electrical communication with the patient's heart 12 by way of an implantable right ventricular lead 30 having, in this embodiment, an RV tip electrode 32, an RV ring electrode 34, an RV coil electrode 36, and a superior vena cava (SVC) coil electrode 38 (also known as a right atrial (RA) coil electrode). Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
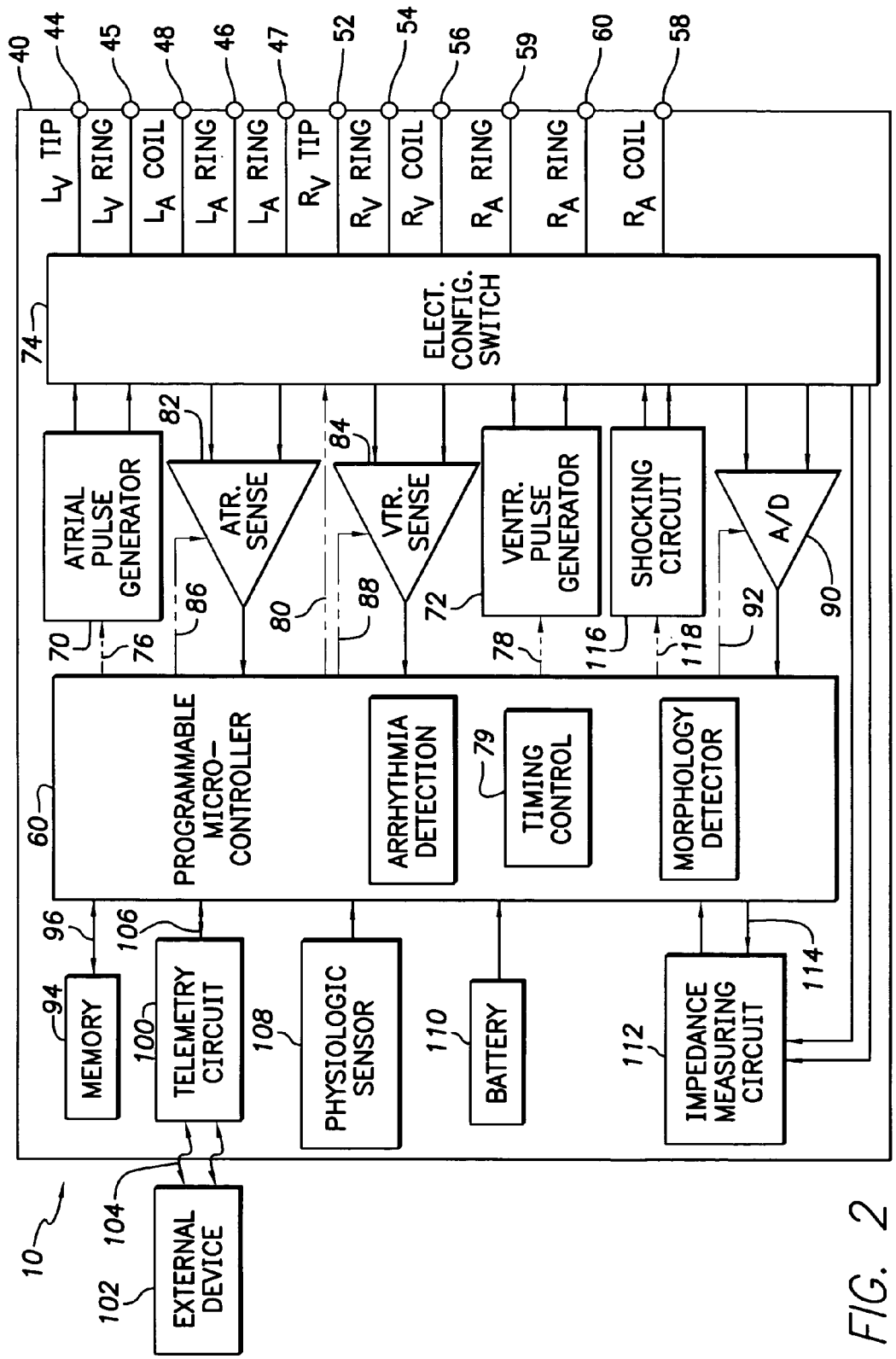
FIG. 2 is a functional block diagram of the multi-chamber implantable stimulation device of FIG. 1 illustrating the basic elements of the stimulation device which can provide cardioversion, defibrillation and pacing stimulation in four chambers of the heart.

FIG. 2 illustrates a simplified block diagram of the exemplary multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 29, 36 and 38 of FIG. 1, for shocking purposes. The housing 40 further includes a connector (not shown) having a plurality of terminals, 44, 45, 46, 47, 48, 52, 54, 56, 58, 59 and 60 (shown schematically and, for convenience, the names of the electrodes to which they are connected are shown next to the terminals). As such, to achieve right atrial sensing and pacing, the connector includes, for example, a pair of right atrial ring terminals 59 and 60 that are respectively adapted for connection to first right atrial (RA) ring electrode 13 and second RA ring electrode 14.

To achieve left chamber sensing, pacing and shocking, the connector includes, for example, a left ventricular tip terminal 44, a left ventricular ring terminal 45, a pair of left atrial ring terminals 46 and 47, and a left atrial shocking terminal 48, which are adapted for connection to the LV tip electrode 26, the LV ring electrode 25, first LA ring electrode 27 and second LA ring electrode 28, and LA coil electrode 29, respectively.

To support right chamber sensing, pacing and shocking, the connector further includes, for example, a right ventricular tip terminal 52, a right ventricular ring terminal 54, a right ventricular shocking terminal 56, and an SVC shocking terminal 58, which are adapted for connection to the RV tip electrode 32, RV ring electrode 34, the RV coil electrode 36, and the SVC coil electrode 38 (also know as RA coil electrode 38), respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein. The use of microprocessor-based control circuits for performing timing and data analysis functions are well known in the art.

Representative types of control circuitry that may be used herein include the microprocessor-based control system of U.S. Pat. No. 4,940,052 (Mann et al.) and the state-machines of U.S. Pat. Nos. 4,712,555 (Thornander et al.) and 4,944,298 (Sholder). For a more detailed description of the various timing intervals used within the stimulation device and their inter-relationship, see U.S. Pat. No. 4,788,980 (Mann et. al.). The '052, '555, '298 and '980 patents are incorporated herein by reference.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74 (also referred to as switch bank 74). It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which are well known in the art.

The switch bank 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not specifically shown).

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. For a complete description of a typical sensing circuit, see U.S. Pat. No. 5,573,550, entitled "Implantable Stimulation Device having a Low Noise, Low Power, Precision Amplifier for Amplifying Cardiac Signals" (Zadeh et al.), which is incorporated herein by reference. The outputs of the atrial and ventricular sensing circuits, 82 and 84, are connected to the microcontroller 60 which, in turn, is able to independently trigger or inhibit the atrial and ventricular pulse generators, 70 and 72, respectively, in a demand fashion in response to the absence or presence of cardiac activity, respectively, in the appropriate chambers of the heart. The sensing circuits, 82 and 84, in turn, receive control signals over signal lines, 86 and 88, from the microcontroller 60 for purposes of controlling the gain, threshold, the polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is the receipt or noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (e.g., bradycardia, normal, low rate VT, high rate VT, and fibrillation rate zones) and various other characteristics (e.g., sudden onset, stability, physiologic sensors, morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller 60, or other detection circuitry, for detecting an evoked response from the heart 12 in response to an applied stimulus, thereby aiding in the detection of "capture." Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. Preferably, a capture threshold search is performed once a day during at least the acute phase (e.g., the first 30 days after implantation of the ICD) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Kleks et al.), which patents are incorporated herein by reference.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. The stimulation device 10 has the ability to sense and store a relatively large amount of data (e.g., from the data acquisition system 90), which data may then be used for subsequent analysis to select, for example, a pacing configuration, as described below.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. If the stimulation device 10 employs shocking therapy, then the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most current devices.

As further shown in FIG. 2, the device 10 is shown as having an impedance measuring circuit 112 which is enabled by the microcontroller 60 via a control signal 114. The known uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used.

If stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial (LA) coil electrode 29, the RV coil electrode 36, and/or the SVC coil electrode 38. As noted above, the housing 40 may act as an active electrode in combination with the RV coil electrode 36, or as part of a split electrical vector using the SVC coil electrode 38 or the LA coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 540 joules), delivered asynchronously (since R-waves may be too disorganized to detect), and pertaining exclusively to the treatment of fibrillation. Accordingly, the microcontroller 60 is capable of controlling the synchronous or asynchronous delivery of the shocking pulses.

II. Discussion of Tachycardias

The following is a brief review the basic electrophysiological mechanisms responsible for ventricular tachycardias (VTs).

During a normal cardiac cycle, a cardiac cell membrane depolarizes and repolarizes in a characteristic fashion known as the action potential. Action potential propagation occurs when depolarization in one cell generates current to neighboring cells, forcing membrane sodium channels to open and allowing a rapid excitatory influx of sodium that further depolarizes the membrane. Sodium channels then close. Other ionic currents repolarize the membrane to its resting state over a slow time course that is sufficiently long for sodium channels to recover excitability. Heart rate is important in this process because the interval between recovery in one cycle and activation in the next provides time for the cell to achieve ionic, metabolic and energetic equilibrium.

When cells die in a myocardial infarct, they electrically uncouple from neighboring viable cells, making the infarct completely unexcitable. Intrinsic or paced wavefronts encountering such an obstacle generally split into two components that collide and recombine on the opposite side of the infarct. When tissue adjacent to the infarct excites prematurely, however, reentry can result if one of the wavefronts blocks in a region with reduced excitability, i.e. incomplete sodium channel opening. The reduced excitability can result from inhomogeneities in membrane properties, geometric changes that increase the wavefront's electrical load, or incomplete recovery of excitability during a short interval. When blocking of one wavefront occurs, the other wavefront may be able to reenter the initial block site, causing was in known as a "reentrant circuit." Action potentials will continually propagate around the infarct at a rate considerably faster than the heart's intrinsic rate provided the reentrant wavefront, i.e. the head, moves slowly enough that tissue ahead recovers excitability, i.e. a tail can form. The spatial extent of inexcitable tissue in this circuit is termed the reentrant wavelength, and is approximated by the product of the head's velocity and the action potential duration. As long as the wavelength is less than the obstacle's perimeter, i.e. the reentrant path length, the head and tail remain separated by an excitable gap. Termination of anatomic reentry requires elimination of the excitable gap, which can be achieved by appropriate pacing. An appropriately timed stimulus (i.e., a pacing pulse) will initiate action potentials that propagate in both directions, colliding with the head and blocking in the tail.

In more simplified terms, the reentrant circuit can be thought of as a conduction wavefront propagating along a tissue mass of somewhat circular geometry. This circular conduction will consist of a portion of refractory tissue and a portion of excitable tissue. To terminate the circuit, a pacing stimulus should be provided at the time and location when the tissue just comes out of refractoriness. If this occurs, the paced stimulation wavefront proceeds toward the advancing wavefront of the circuit, colliding with the wavefront and interrupting the circuit. If the pacing stimulus (i.e., pacing pulse) arrives too soon it will be ineffective because the tissue will still be in refractoriness. If the stimulus arrives too late, it will generate wavefronts both towards the advancing wavefront and towards the tail of the circuit. Although one pacing generated wavefront will collide with the advancing wavefront of the reentrant circuit and will halt is progress, the latter pacing generated wavefront will act to sustain the reentrant circuit.

Accordingly, the probability of ATP succeeding in terminating the VT is related to the ability of the pacing stimulation wavefront to arrive at the location of the reentrant circuit (e.g., within a myocardium) in such a manner that the reentrant circuit is modified or interrupted. Factors influencing this process include the distance of the pacing electrode(s) from the reentrant circuit, the pacing stimulus energy, and the timing of the pacing stimuli relative to the conduction velocities and refractory periods of the myocardium.

There are several different pacing modalities which have been suggested for termination of tachycardia. The underlying principle in all of them is that if a pacing stimuli stimulates the heart at least once shortly after a heartbeat, before the next naturally occurring heartbeat at the rapid rate, the heart may successively revert to sinus rhythm. Tachycardia is often the result of electrical feedback within the heart; a natural beat results in the feedback of an electrical stimulus which prematurely triggers another beat. By appropriately interposing a stimulated heartbeat, the stability of the feedback loop is disrupted.

Referring back to FIG. 1, exemplary pacing device 10 is shown as including many electrodes. For example, in the right ventricle there are the RV coil 36, the RV ring 34, and the RV tip 32. In the coronary sinus, there is a pair of left atrial (LA) rings 27 and 28, the LV ring 25, and the LV tip 26. In the right atrium is the right atrial (RA) coil 38 and a pair of RA rings 13 and 14. The present disclosure uses these electrodes to sense signals.

III. Determination of Proximity of Pacing Site to Reentrant Circuit

It has been observed that the electrical source of the wavefront in the proximity of the reentrant circuit is similar to an electrical dipole layer, where the closer a sensing electrode is to the wavefront the stronger the sensed signal and the greater the rate of change (slope or slew rate) of the sensed signal. According to an embodiment, as discussed below with reference to FIG. 3, pacing pulses are produced using the electrode(s) closest to the reentrant loop to attempt to convert a ventricular tachycardia or VT to normal sinus rhythm SR. Consequently, RV and LV can be paced independent of one another. Thus, during ventricular tachycardia the cardiac signal is sensed (e.g., unipolar sensing) at each pacing site in the ventricle. The proximity of the pacing sites to the reentrant circuit is then determined using the one or more embodiments disclosed herein. ATP therapy can then be delivered by the pacing site closest to the reentrant circuit.

Figure 3:
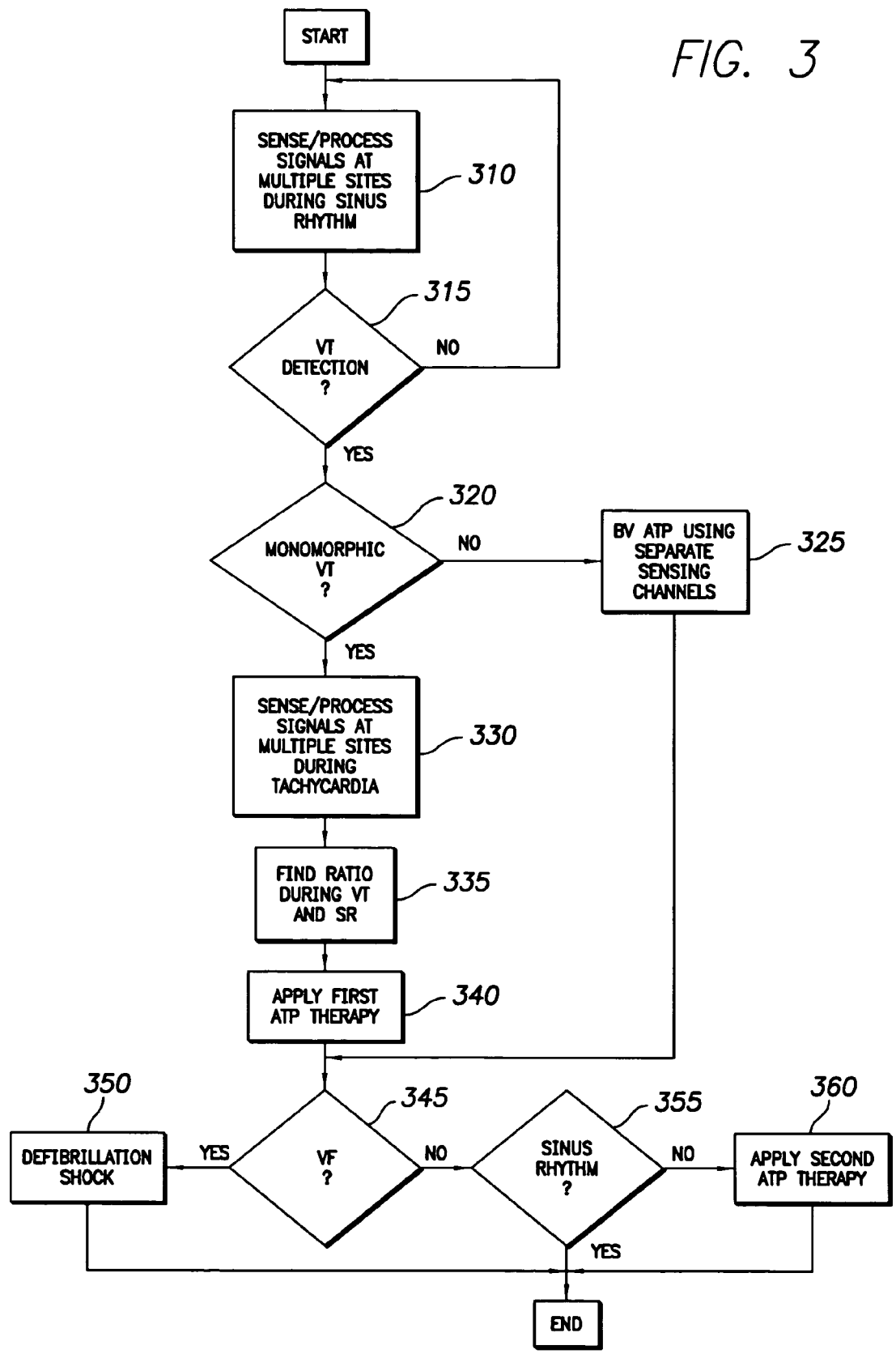
FIG. 3 is a flow diagram illustrating an exemplary method for determining the proximity of a pacing site to a reentrant circuit during ventricular tachycardia and applying ATP pulses, according to one embodiment.

FIG. 3 is a flow diagram illustrating an exemplary method for determining the proximity of a pacing site to a reentrant circuit during ventricular tachycardia and applying ATP pulses, according to one embodiment. The method may be implemented by the stimulation device 10 (FIG. 2) or a similar device. The method of FIG. 3 is illustrated in flow chart form. In this flow chart, and the other flow charts described herein, the various algorithmic steps are summarized in individual "blocks." Such blocks describe specific actions or decisions that are carried out as the algorithm proceeds. Where a microcontroller (or equivalent) is employed, the flow charts presented herein provide the basis for a "control program" that may be used by such a microcontroller (or equivalent) to effectuate the desired control of the pacing device.

While this exemplary embodiment is described with respect to ventricular tachycardia, a similar technique may be employed (perhaps simultaneously) for atrial tachycardia. It should further be noted that while FIG. 2 shows two electrodes in the ventricle (LV and RV) and two electrodes in the atrial (LA and RA), additional electrodes (and/or sites) may be utilized in one or both ventricles, one or both atria, or other locations. It should further be noted the term "electrodes implanted in the left ventricle" is meant to include, for example, electrodes on the epicardium of the left ventricle, such as in the cardiac veins of the left ventricle; thus, for example, the left-side lead may be placed transvenously into the left-side chamber, transvenously into a cardiac vein in electrical contact with the left-side chamber, or placed epicardially.

Referring to FIG. 3, the method 300 included block 310 in which the peak and/or the slope (or slew rate) of the cardiac signal at each site (the heart's left and right ventricles, LV and RV) for a sinus rhythm cycle are sensed (hereinafter also referred to as "sensed values") and stored in memory (e.g., RAM, Flash memory, etc.). The sensed values for the previous N cycles may also be stored in memory, where "N" may be any positive whole number equal to 1 or greater (e.g., 5). In addition, a trailing average of each sensed value for the previous N cycles may be calculated and stored in memory. The sensed cardiac signals may be processed (in a similar fashion described below with respect to block 330).

The flow then moves to block 315 where it is determined whether VT has been detected. Conventional methods of detecting VT may be employed. If VT is not detected, the flow moves back to block 310 where the peak and/or slope of the cardiac signal at each site for the next sinus rhythm cycle are sensed and stored in memory. If VT is detected, block 320 is executed where a determination is made as to whether the sensed cardiac signal is monomorphic. If the sensed cardiac signal during VT is not monomorphic, block 325 is executed where BV ATP is administered simultaneously for the LV and RV. The flow then moves to block 345 to determine whether the patient has entered ventricular fibrillation.

If the cardiac signal during VT is monomorphic (block 320), the flow moves to block 330. At block 330, the cardiac signal is sensed at each site (in this embodiment LV and RV) and the sensed signals are processed to provide an indicia representative of the cardiac signal. For example, the sensed signal is processed to determine a peak and/or slope of the cardiac signal at each site. This may occur for one or more cycles. If the cardiac signal is processed over two or more cycles, the average and/or maximum of the processed signal(s) may be taken. These values may be stored in memory.

There are several ways in which the sensed cardiac signals are processed to provide an indicia representative of the cardiac signals. In one embodiment, the peak of each cardiac signal is determined by taking the maximum intrinsic deflection, which is a value equal to the maximum and minimum of the cardiac signal in one cycle (e.g., between R wave and S). In another embodiment, the peak is determined by taking the derivative of the cardiac signal to find the maximum and minimum points of the cardiac signal and then determining the value(s) of the cardiac signal therefrom. In yet another embodiment, the peak is determined by taking the maximum value of any peak, negative or positive, during a cardiac cycle (e.g., peak of the R wave). In yet a further embodiment, the cardiac signal is processed by determining the maximum derivative (e.g., the difference of the signals between two time points). A similar processing may be conducted for cardiac signals sensed during sinus rhythm (e.g., at block 310). This processing of the cardiac signals sensed during sinus rhythm may be conducted prior to execution of block 330 (e.g., at block 310).

Once the cardiac signals (sensed during VT) are processed at block 330, block 335 is executed. At block 335, the ratio of the sensed and processed cardiac signals during VT and SR is determined at each site. In the case where the peak of the cardiac signal is detected (e.g., maximum intrinsic deflection, maximum peak whether positive or negative, etc.), the site that has the largest value of the ratio is considered the site (of the electrode) that is closest to the reentrant circuit. In the case where the slew rate (e.g., the maximum change of the signals between two fixed points) of the cardiac signal is determined, the site that has the shortest time indicates the site that is closest to the reentrant circuit. In an optional embodiment, not shown in FIG. 3, if the ratio of the signals between the sites is very small (e.g., below a predetermined epsilon or threshold), block 325 may be executed to administer simultaneous BV ATP through the separate sensing/pacing channels.

At block 340, rather than generating simultaneous right ventricle and left ventricle pulses (i.e., simultaneous bi-ventricular pulses), ATP therapy is applied using the site closest to the reentrant circuit. In one embodiment, ATP therapy is applied by providing a plurality of pacing pulses using the site closest to the reentrant circuit. The timing of each pacing pulse during a cardiac cycle may be determined as described below with reference to FIG. 4. It should be noted that any other type of ATP therapy may be applied including those well known to skilled in the art.

Once ATP therapy is applied at block 340, the method, at block 345, determines whether the patient has entered ventricular fibrillation. This determination may be made by techniques well know to those skilled in the art. If ventricular fibrillation is present, block 350 is executed where defibrillation shocks are delivered to the patient.

If, on the other hand, the patient has not entered ventricular fibrillation, block 355 is executed where a determination is made as to whether the ventricular tachycardia has been converted into normal sinus rhythm, SR. If so, the process ends (or moves back to block 310). If the tachycardia persists, the flow moves to block 360 where a second ATP therapy is applied to the patient. In one embodiment, the second ATP therapy is applied using the electrode second closest to the reentrant circuit. In another embodiment, the second ATP therapy is applied using all sites. Other variations exist. For example, if the second ATP therapy is applied using the second closest site and that does not end VT, then a third ATP therapy may be applied using all sites.

In this embodiment, the cardiac signals at each site, both during SR and VT, are sensed using unipolar sensing. In this regard, a first pair of electrodes are shorted together to produce a unipolar electrode. The anti-tachycardia pacing pulses may also be delivered to the first pacing site using the shorted together first pair of electrodes. With respect to the embodiment of FIG. 3, the first pair of electrodes may include, for example, a left ventricular (LV) tip electrode and a LV ring electrode. Similarly, a second pair of electrodes can be shorted together to sense the cardiac signal. Anti-tachycardia pacing pulses may be delivered to the second pacing site using the shorted together second pair of electrodes. The second pair of electrodes may include, for example, a right ventricular (RV) tip electrode and a RV ring electrode. In another embodiment, the RV tip electrode, the RV ring electrode, and a RV coil electrode are all shorted together to produce an even larger electrode. The anti-tachycardia pacing pulses could then be delivered to the right ventricle using the shorted together RV tip, ring, and coil electrodes. The shorting can be performed, for example, within the electrode configuration switch 74. As mentioned above, electrode switch 74 can be controlled by microcontroller 60, via control signal 80. Unipolar sensing minimizes the effects of electrode orientation. The shorted unipolar pacing lead will stimulate many more cardiac cells, thereby increasing the chance of crossing through the wavefronts to terminate the tachycardia. In another embodiment, bipolar pacing and sensing may be used. One potential drawback to bipolar pacing is that the "reach" of the electric field is relatively small because it is tightly confined between the two electrodes of an electrode pair (e.g., the LV pair or RV pair).

A potential problem with unipolar pacing is that the current from the can to the pacing electrodes can result in pocket stimulation at the site of the can (i.e., stimulation of muscle tissue surrounding the can). Pocket stimulation, although not dangerous, can be uncomfortable to a patient. In an embodiment, pacing pulses generated by a unipolar LV electrode (e.g., produced by shorting together LV ring 25 and LV tip 26) have an opposite polarity than pacing pulses generate by an RV unipolar electrode (e.g., produced by shorting together the RV ring 54 and RV tip 52) when performing BV ATP. This would result in an almost zero net current flowing from the can, when the LV unipolar electrode pulses and RV unipolar electrode pulses are delivered simultaneously.

In one embodiment, the polarity of each unipolar electrode is constant and opposite the other unipolar electrode. In another embodiment, the polarity of a first unipolar electrode (e.g., produced by shorting together LV ring 25 and LV tip 26) alternates between a first polarity (e.g., positive) and a second polarity (e.g., negative), while the polarity of a second unipolar electrode (e.g., produced by shorting together RV ring 54 and RV tip 52) alternates between the second polarity (e.g., negative) and the first polarity (e.g., positive) such that each unipolar electrodes always has the opposite polarity of the other unipolar electrode. In other words, opposite polarities are used at different sites (e.g., the left ventricle and the right ventricle). The alternating could happen on a pulse by pulse basis. Alternatively, the alternating could happen on a pulse burst by pulse burst basis.

IV. Determination of Excitable Gap Time Location

The effectiveness of ATP therapy in terminating tachycardias is dependent, at least in part, on the timing of the ATP pacing pulses delivered. The ATP therapy is most effective in terminating tachycardias when administered during a window of time prior to the beginning of the next QRS cycle commonly referred to as the "excitable gap." Conventional ATP therapy typically utilizes a percentage of the VT cycle length (such as 85%) in delivering pacing pulses synchronized with the next QRS. It should be noted that this percentage of the cycle length in delivering ATP therapy is based on empirical data and is not patient or rhythm specific.

Figure 4:
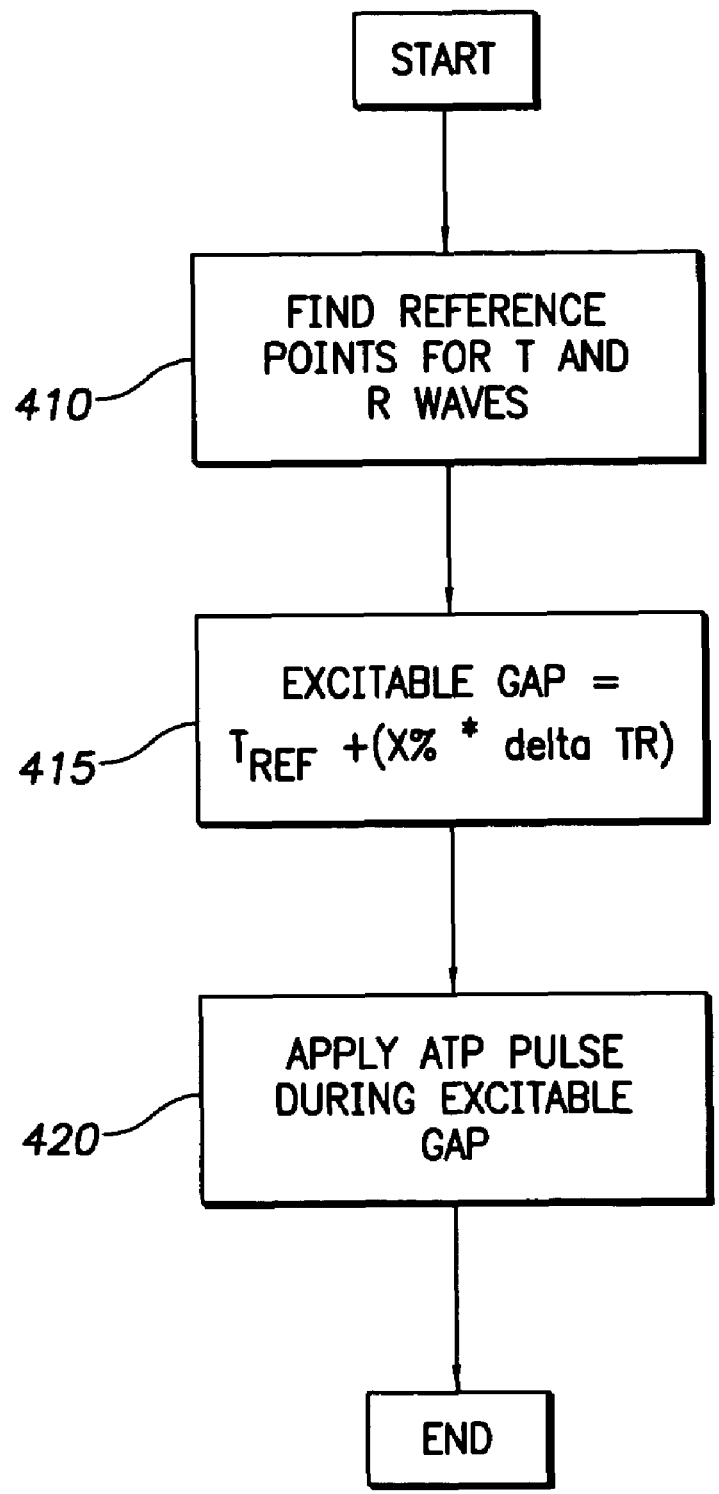
FIG. 4 is a flowchart describing a method for determining the excitable gap of a cardiac cycle for delivering an ATP pulse, according to an embodiment.

Another approach involves T-wave and/or R-wave detection using a wide band amplifier or similar technique. In one exemplary implementation, as shown in FIG. 4, reference points of the T and R waves are determined for each VT cycle (block 410). In one embodiment, the reference points are taken at the end of the T wave (Tend) and the beginning of the R wave ($R_{beg}$). $R_{beg}$ is the timing of the sensed QRS at programmed sensitivity. The time difference between these two reference points, ATR, is then determined. The excitation gap is a percentage (x %) of this time difference after the T wave, as expressed below (block 415):

$$\text{Excitation gap} = T_{end} + (x\% * \Delta TR) \qquad (1)$$

In one or more embodiments, "x" is between 20 and 80 percent of ΔTR. However, "x" can take on other values. It should be noted that other reference points of the T and R waves may be used such as the peaks ($T_{peak}$ and $R_{peak}$).

At block 420, an ATP pulse is delivered during the excitable gap determined at block 415. Using the time difference between the T and R waves to determine the excitable gap corrects for time variations. Equation (1) may be used to calculate the excitable gap for both the RV and LV independently. Moreover, equation (1) may be used to calculate the excitable gap for both LA and RA independently in the case of atrial tachycardia.

The peak or other reference point of the T wave may be determined using a time assembly average method or the technique disclosed in copending patent application Ser. No. 10/045,495 filed Oct. 19, 2001, entitled "Anti-Tachycardia Pacing Methods and Devices," assigned to the assignee of the present application, the contents of which are fully incorporated herein by reference.

To detect the reference points of the T wave including the peak ($T_{peak}$), a bandpass filter may be utilized. In one embodiment, the bandpass filter frequency range is 1-250 Hz. Other frequency ranges may be utilized. With reference to FIG. 2, the bandpass filter may be part of the electrode configuration switch 74 or external to it such as between the electrode configuration switch 74 and the A/D converter 90.

Furthermore, embodiments discussed above have been primarily described as methods with reference to flow charts. Embodiments may also be directed to devices (also referred to as apparatuses) that perform the features discussed above. For example, embodiments may also be directed to a microprocessor (e.g., microprocessor 60) that performs the features described herein. Additionally, an embodiment is also directed to an implantable device (e.g., pacing device 10) that includes a microprocessor for performing such features. Further, an embodiment may also be directed to systems that perform the features discussed above. Such a system can be, for example, an external processor in communications with a microprocessor of an implantable device.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method for anti-tachycardia pacing, comprising:
   sensing, during sinus rhythm, first and second cardiac signals at first and second sites, respectively, in a patient's heart;
   sensing, during tachycardia, third and fourth cardiac signals at said first and second sites, respectively;
   processing said first and second cardiac signals to provide first and second values, respectively, and processing said third and fourth cardiac signals to provide third and fourth values, respectively;
   comparing the first and third values and the second and fourth values; and
   delivering one or more anti-tachycardia pacing pulses at one of said first and second sites based on said comparing of said values.

2. The method of claim 1 further comprising:
   delivering one or more anti-tachycardia pacing pulses at said other of said first and second sites if the tachycardia has not been terminated.

3. The method of claim 1 wherein:
   sensing, during sinus rhythm, comprises sensing, during sinus rhythm, first and second signals at a left ventricle and a right ventricle, respectively, in said patient's heart; and
   sensing, during tachycardia, comprises sensing, during ventricular tachycardia, third and fourth signals at said left ventricle and said right ventricle, respectively.

4. The method of claim 1 wherein:
   sensing, during sinus rhythm, comprises sensing, during sinus rhythm, first and second signals at a left atrial and a right atrial, respectively, of said patient's heart; and
   sensing, during tachycardia, comprises sensing, during atrial tachycardia, third and fourth signals at said left atrial and said right atrial, respectively.

5. The method of claim 1 wherein sensing, during sinus rhythm, comprises sensing said first signal at said first site using a first pair of electrodes and sensing said second signal at said second site using a second pair of electrodes.

6. The method of claim 1 wherein delivering comprises:
delivering one or more anti-tachycardia pacing pulses, in relation to T and R waves, at one of said first and second sites based on said comparing of said first and second ratios.

7. The method of claim 1 wherein:
processing comprises determining a peak of each of said first and second cardiac signals to provide first and second peak values, respectively, and each of said third and fourth cardiac signals to provide third and fourth peak values, respectively;
comparing comprises comparing a first ratio of the first and third peak values and a second ratio of the second and fourth peak values; and
delivering one or more anti-tachycardia pacing pulses at said first site if said first ratio is greater than said second ratio and alternatively at said second site if said second ratio is greater than said first ratio.

8. The method of claim 1 wherein:
processing comprises determining a slew rate of each of said first and second cardiac signals to provide first and second values, respectively, and each of said third and fourth cardiac signals to provide third and fourth values, respectively.

9. An implantable cardiac stimulation device configured to control a plurality of electrodes to be implanted in a respective chamber of a patient's heart, comprising:
a pulse generator coupled to the plurality of electrodes to independently generate stimulation pulses to stimulate an associated chamber in the patient's heart;
a sensing circuit coupled to the plurality of electrodes to independently receive cardiac signals from an associated chamber in the patient's heart;
a controller coupled to said pulse generator and sensing circuit, configured to:
(1) process first and second cardiac signals received during sinus rhythm from first and second chambers, respectively, to provide first and second values, respectively,
(2) process third and fourth cardiac signals received during tachycardia from said first and second chambers, respectively, to provide third and fourth values, respectively,
(3) compare a first ratio of said first and third values and a second ratio of said second and fourth values, and
(4) deliver one or more anti-tachycardia pacing pulses at one of said first and second chambers based on (3).

10. The implantable cardiac stimulation device of claim 9 wherein said controller is configured to deliver one or more anti-tachycardia pacing pulses at said other of said first and second chambers if the tachycardia has not been terminated.

11. The implantable cardiac stimulation device of claim 9 wherein said first and second chambers comprise left and right ventricles, respectively, in the patient's heart, and said tachycardia comprises ventricular tachycardia.

12. The implantable cardiac stimulation device of claim 9 wherein said first and second chambers comprise left and right atria, respectively, in the patient's heart, and said tachycardia comprises atrial tachycardia.

13. The implantable cardiac stimulation device of claim 9, wherein said controller is configured to:
process said first and second signals by determining a peak of said first and second signals to provide first and second peak values, respectively; and
process said third and fourth signals by determining the peak of said first and second signals to provide third and fourth peak values, respectively.

14. The implantable cardiac stimulation device of claim 13 wherein:
said controller is configured to determine said peak of said first and second signals, and said peak of said third and fourth signals by performing at least one of the following: determining a maximum intrinsic deflection of each signal, determining a maximum of a positive peak of each signal, and determining a maximum peak, whether positive or negative, of each signal.

15. The implantable cardiac stimulation device of claim 9, wherein said controller is configured to:
process said first and second signals by determining a slew rate of said first and second signals to provide said first and second values, respectively; and
process said third and fourth signals by determining the slew rate of said first and second signals to provide said third and fourth values, respectively.

16. The implantable cardiac stimulation device of claim 9, wherein said pulse generator and said sensing circuit are coupled to a first pair of electrodes to be located in said first chamber and a second pair of electrodes to be located in said second chamber.

17. The implantable cardiac stimulation device of claim 16, wherein said first pair of electrodes is shorted together and said second pair of electrodes is shorted together.

18. The implantable cardiac stimulation device of claim 9, wherein said controller is configured to deliver one or more anti-tachycardia pacing pulses at said first chamber if said first ratio is greater than said second ratio and alternatively at said second chamber if said second ratio is greater than said first ratio.

19. The implantable cardiac stimulation device of claim 9, wherein said controller is configured to:
process a first plurality of signals and a second plurality of signals received during a plurality of sinus rhythm cycles at said first and second chambers, respectively, to provide a first plurality of values and a second plurality of values, respectively;
determine an average of said first plurality of values and said second plurality of values to provide a first average value and a second average value, respectively; and
compare said first ratio of said first average value and said third value and said second ratio of said second average value and said fourth value.

20. The implantable cardiac stimulation device of claim 9 wherein said controller comprises a central processing unit.

21. An apparatus, comprising:
a plurality of pairs of electrodes for implanting in a respective plurality of sites in a patient's heart; and
an implantable cardiac stimulation device coupled to said plurality of pairs of electrodes, comprising:
a pulse generator circuit coupled to the plurality of pairs of electrodes,
a sensing circuit coupled to the plurality of pairs of electrodes, and
a controller coupled to said pulse generator and sensing circuits, wherein said controller is configured to (a) process first and second cardiac signals sensed during normal sinus rhythm by said sensing circuit using first and second pairs of electrodes, to provide first and second values, respectively, (b) process third and fourth cardiac signals sensed during tachycardia by said sensing circuit using said first and second pairs of electrodes, respectively, to provide third and fourth values, respectively, and (c) deliver one or more anti-tachycardia pacing pulses using one of said first and second pairs of electrodes based on a comparison of a first ratio of said first and third values and a second ratio of said second and fourth values.

22. The apparatus of claim 21 wherein said controller is configured to deliver one or more anti-tachycardia pacing pulses using said first pair of electrodes if said first ratio is greater than said second ratio and alternatively using said second pair of electrodes if said second ratio is greater than said first ratio.

23. The apparatus of claim 21 wherein said first and second pairs of electrodes are implanted in left and right ventricles, respectively, of the patient's heart.

24. The apparatus of claim 21 wherein said implantable cardiac stimulation device further includes a switch coupled to the pulse generator circuit, sensing circuit, controller, and said first and second pairs of electrodes.

25. The apparatus of claim 24 wherein said controller is configured to control the switch to short together the first pair of electrodes and to short together the second pair of electrodes.

* * * * *